United States Patent [19]

Hermecz et al.

[11] Patent Number: 5,380,845
[45] Date of Patent: Jan. 10, 1995

[54] PROCESS FOR THE PREPARATION OF QUINOLINE CARBOXYLIC ACID DERIVATIVES

[75] Inventors: István Hermecz; Géza Kereszturi; Lelle Vasvári; Agnes Horváth, all of Budapest; Mária Balogh, Dunakeszi; Péter Ritli, Budapest; Judit Sipos, Budapest; Anikó Pajor, Budapest, all of Hungary

[73] Assignee: Chinoin Gyogyszer- ES Vegyeszeti Termekek Gyara RT., Budapest, Hungary

[21] Appl. No.: 149,692

[22] Filed: Nov. 9, 1993

Related U.S. Application Data

[63] Continuation of Ser. No. 340,174, Apr. 10, 1989, abandoned.

[30] Foreign Application Priority Data

Jun. 24, 1987 [HU] Hungary ............................... 2858/87
Jul. 10, 1987 [HU] Hungary ............................... 3146/87

[51] Int. Cl.⁶ .................. C07D 401/02; C07D 401/04
[52] U.S. Cl. ..................................... 544/363; 544/229
[58] Field of Search ............................... 544/363, 229

[56] References Cited

U.S. PATENT DOCUMENTS 4,803,274  2/1989  Hermecz et al. ..................... 546/13
4,806,645  2/1989  Hermecz et al. ..................... 546/13

FOREIGN PATENT DOCUMENTS 0131839    1/1985   European Pat. Off. .
62-294689  12/1987  Japan .
WO87/03586  6/1987  WIPO .
WO87/03587  6/1987  WIPO .

OTHER PUBLICATIONS

J. Med. Chem., 28, 1558 (1985).

*Primary Examiner*—Bernard Dentz
*Attorney, Agent, or Firm*—Herbert Dubno; Jonathan Myers

[57] ABSTRACT

The invention relates to a new process for the preparation of antibacterial compounds of the Formula I

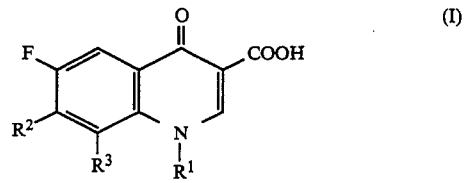

wherein
$R^1$ stands for phenyl substituted by 1 or 2 halogen atoms;
$R^2$ stands for piperazinyl or 4-methyl-piperazinyl;
and pharmaceutically acceptable salts thereof which comprises using a compound of the Formula II

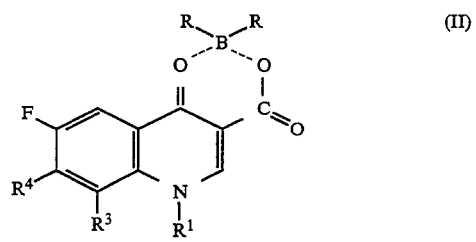

wherein
R stands for halogen or an aliphatic acyloxy group containing 2 to 6 carbon atoms or an aromatic acyloxy group containing 7 to 11 carbon atoms and
$R^4$ stands for fluorine or chlorine as a starting material.

9 Claims, No Drawings

PROCESS FOR THE PREPARATION OF QUINOLINE CARBOXYLIC ACID DERIVATIVES

This is a continuation of copending application Ser. No. 07/340,174 filed on Apr. 10, 1989, now abandoned.

FIELD OF THE INVENTION

This invention relates to a new process for the preparation of 1-substituted-7-(optionally substituted piperazine)-6-fluoro-8-(optionally fluoro-substituted)-4-oxo-1,4-dihydro-quinoline-3-carboxylic acid derivatives of the Formula I

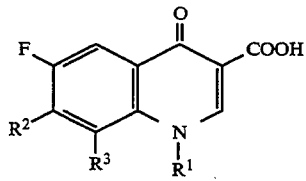

and pharmaceutically acceptable salts thereof.

In the Formula I $R^1$ stands for phenyl being optionally substituted by 1 or 2 halogen atoms, or a group of the Formula —$CH_2CR^6R^7R^8$ (wherein $R^6$, $R^7$ and $R^8$ stand for hydrogen or halogen);

$R^2$ stands for piperazinyl or 4-methyl-piperazinyl;

$R^3$ stands for hydrogen or fluorine.

BACKGROUND OF THE INVENTION

It is known that a group of the 7-substituted-carboxylic derivatives of the Formula I (wherein $R^2$ stands for piperazinyl, 4-methyl-piperazinyl, $R^1$ stands for a group of the Formula —$CH_2CR^6R^7R^8$ (wherein $R^6$, $R^7$ and $R^8$ stand for hydrogen or halogen) and $R^3$ stands for fluorine) possesses high antibacterial activity (J. Med. Chem. 1986, 29, 445; Drugs of Fut. 1984, 9, 246; 23rd Intersci. Conf. Antimicrob. Agents Chemother. 1983, Abst. 658, 7th Int. Symp. Fut. Trends Chemother. 1986, 86). These compounds can be prepared by reacting 6,7,8-trifluoro-4-oxo-1,4-dihydro-quinoline-3-carboxylic acid and cyclic amines (Belgian patent specification 887874, GB patent specification 2057444, Austrian patent specification 537813 and European patent specification 1064489).

Another group of the 7-substituted-quinoline-3-carboxylic acids of the Formula I (wherein $R^1$ stands for phenyl optionally substituted by 1 or 2 halogen atoms, $R^2$ stands for piperazinyl or 4-methyl-piperazinyl and $R^3$ stands for hydrogen) has also high antibacterial activity (24th Intersol. Conf. Antimicrob. Agents Chemother, 1984, Abst. 72-78., Amtimicrob. Agents Chemother. 1987., 619, Antimicrob. Agents Chemother. 1986., 192-208). These compounds can be prepared by reacting 1-substituted phenyl-6-fluoro-7-chloro-4-oxo-1,4-dihydro-quinoline-3-carboxylic acid and cyclic amines in the presence of a solvent at a temperature of 100° C. for 20 hours (European patent specification 131839, J. Med. Chem. 1985, 1558., J. Med. Chem. 1987. 504.).

SUMMARY OF THE INVENTION

According to the present invention there is provided a new process for the preparation of quinoline-3-carboxylic acid derivatives of the Formula I (wherein $R^1$ stands for phenyl optionally substituted by 1 or 2 halogen atoms, or a group of the Formula —$CH_2CR^6R^7R^8$ (wherein $R^6$, $R^7$ and $R^8$ stand for hydrogen or halogen), $R^2$ stands for piperazinyl, 4-methyl-piperazinyl and $R^3$ stands for hydrogen or fluorine) and pharmaceutically acceptable salts thereof which comprises reacting a compound of the Formula II

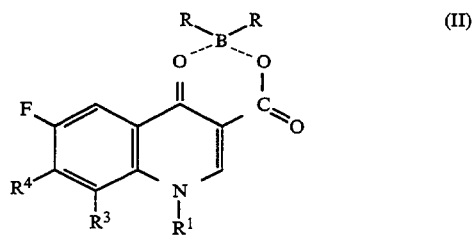

wherein R stands for halogen, an aliphatic acyloxy group containing 2 to 6 carbon atoms or aromatic acyloxy group containing 7 to 11 carbon atoms, $R^4$ stands for fluorine or chlorine, $R^1$ and $R^2$ are as stated above with an amine of the Formula III

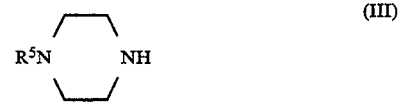

wherein $R^5$ stands for hydrogen or methyl or a salt thereof and subjecting the compound of the Formula IV

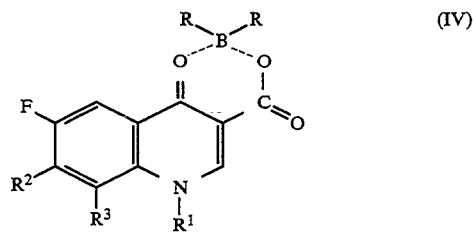

thus obtained wherein R, $R^1$, $R^2$ and $R^3$ are as stated above to hydrolysis after or without isolation and if desired converting the compound of the Formula I thus obtained into a salt thereof or setting free the same from its salt.

The advantage of the process of the present invention is that it enables the preparation of the compounds of the Formula I in a simple manner, with very high yields and in a short reaction time.

The boron derivatives of the Formula IV are new compounds.

According to a preferred form of realization of the process of the present invention the boron derivative of the Formula IV is converted into the desired quinoline-3-carboxylic acid of the Formula I without isolation.

The boron derivatives of the Formula II can be reacted with the amine of the Formula III if desired in the presence of an inert organic solvent and an acid binding agent.

As inert organic solvent preferably an acid amide (e.g. dimethyl formamide, dimethyl acetamide), a ketone (e.g. acetone, methyl ethyl ketone), an ether (e.g. dioxane, tetrahydrofuran, diethyl ether), an ester (e.g. ethyl acetate, methyl acetate, ethyl propionate), a sulfoxide (e.g. dimethyl sulfoxide), an alcohol (e.g. methanol, ethanol, 1-decanol, butanol) may be used.

As acid binding agent an organic or inorganic base may be used. From the group of organic bases trialkyl amines (e.g. triethyl amine, tributyl amine), cyclic amines (e.g. pyridine, 1,5-diazabicyclo(5,6,0)undec-5-ene, 1,5-diazabicyclo(4.3.0)-non-5-ene, 1,4-diazabicyclo(2.2.2)octane) can be mentioned, while as inorganic base preferably hydroxides or carbonates of alkali or alkaline earth metals can be applied. Thus as acid binding agent advantageously potassium carbonate, potassium hydrogen carbonate, sodium hydroxide, calcium hydroxide, etc. or an excess of the amine of the Formula III can be used.

The boron derivative of the Formula II and the amine of the Formula III can be reacted at a temperature between 0° and 200° C., depending on the solvent used. The reaction time may vary between half an hour and 10 hours. The reaction time depends on the reaction temperature, too. If the reaction is carried out at higher temperature, the reaction time can be shortened. The above reaction conditions are preferable values and other conditions may be used as well.

The compounds of the Formula IV can be hydrolyzed to the desired quinoline-3-carboxylic acids of the Formula I, after or without isolation, under acidic or basic conditions. The compound of the Formula IV precipitates from the reaction mixture e.g. on cooling and can be separated e.g. by filtration or centrifuging, if desired.

Basic hydrolysis may be preferably carried out by heating, with the aid of a hydroxide or carbonate of an alkali metal or an alkaline earth metal hydroxide, used as aqueous solution. One may preferably use an aqueous solution of sodium hydroxide, potassium hydroxide, sodium carbonate, potassium carbonate, calcium hydroxide. However, organic amines (e.g. triethyl amine) may also be applied in the hydrolysis step.

Acidic hydrolysis may preferably be accomplished by using an aqueous mineral acid. One may preferably proceed by hydrolysing a compound of the Formula IV by heating with an aqueous solution of hydrochloric acid, hydrogen, bromide, sulfuric acid or phosphoric acid. Hydrolysis may also be accomplished with the aid of an organic acid (e.g. acetic acid, propionic acid, etc.).

Hydrolysis of the compounds of the Formula IV may also be carried out in aqueous medium in the presence of a water-miscible organic solvent. For this purpose e.g. alcohols (e.g. methanol, ethanol), a ketone (e.g. acetone), an ether (e.g. dioxane), an acid amide (e.g. dimethyl formamide), a sulfoxide (e.g. dimethyl sulfoxide), or pyridine may be used.

The quinoline-3-carboxylic acid of the Formula I thus obtained may be isolated e.g. adjusting the pH value of the aqueous solution to a suitable value and separating the precipitated crystals e.g. by filtration or centrifuging or by lyophylizing the aqueous reaction mixture.

The compounds of the Formula I can be converted into pharmaceutically acceptable salts thereof in a known manner. Thus preferably acid addition salts can be formed, e.g. salts formed with hydrogen halides, sulfonic acids, sulfuric acid or organic acids. One may form preferably chlorides, bromides, aryl sulfonates, methane sulfonates, maleares, fumarates, benzoates, etc. The compounds of the Formula I form salts with alkali or alkaline earth metals or other metal ions as well.

Accordingly the sodium, potassium, magnesium, silver, copper salts, etc. may be prepared.

The compounds of the Formula I and pharmaceutically acceptable salts thereof can be converted into hydrates (e.g. hemihydrates, trihydrates, etc.) by methods known per se.

According to a further aspect of the present invention there are provided new compounds of the Formula IV (wherein R, $R^1$, $R^2$ and $R^3$ are as stated above).

The starting materials of the Formula II can be prepared by reacting 1-phenyl-6-fluoro-7-chloro-4-oxo-1,4-dihydro-quinoline-3-carboxylic acid (European patent specification 131.839) or 1-ethyl-6,7,8-trifluoro-4-oxo-1,4-dihydroquinoline-3-carboxylic acid (GB patent specification 2.057.440) with a boron derivative (e.g. with a compound of the Formula V

wherein R is halogen or an aliphatic acyloxy group containing 2 to 6 carbon atoms or an aromatic acyloxy group containing 7 to 11 carbon atoms) or with fluoroborate in aqueous or in organic medium.

Further details of the present invention are to be found in the following Examples without limiting the scope of protection to the said Examples.

EXAMPLE 1

1.59 g of (1-ethyl-6,7,8-trifluoro-1,4-dihydro-4-oxo-quinoline-3-carboxylate-$O^3,O^4$)-difluoro-boron are reacted with 1.29 g of piperazine in 8 ml of dimethyl sulfoxide at 100° C. for 3 hours. A 6 w/v % aqueous solution of 12.6 ml of sodium hydroxide are added and hydrolysis is carried out by heating for 2 hours. The reaction mixture is filtered, the pH value is adjusted to 7 with 96 w/v % acetic acid and diluted with 15 ml of water. The crystalline reaction mixture is cooled overnight and the precipitated crystals are filtered, washed with water and dried. Thus 1.61 g of 1-ethyl-6,8-difluoro-1,4-dihydro-4-oxo-7-piperazino-quinoline-3-carboxylic acid are obtained. M.p. is 234°–236° C.

Analysis for the Formula $C_{16}H_{17}F_2N_3O_3$: Calculated: C=56.90% H=5.07% N=12.45% Found: C=56.75% H=5.02% N=12.48%.

EXAMPLE 2

1.99 g of (1-ethyl-6,7,8-trifluoro-1,4-dihydro-4-oxoquinoline-3-carboxylate-$O^3,O^4$)-bis(diacetate-O)-boron are reacted with 1.29 g of piperazine in 8 ml of dimethyl sulfoxide at 110° C. for 2 hours. A 3 w/v % aqueous solution of 20 ml of 3 w/v % sodium hydroxide are added. The reaction mixture is refluxed for an hour whereupon filtered and the pH value is adjusted to 7 with 96 w/v % acetic acid. After cooling and diluting with 10 ml of water the precipitated crystals are filtered and dried. Thus 1.59 g of ochre colored 1-ethyl-6,8-difluoro-1,4-dihydro-4-oxo-7-piperazino-quinoline-3-carboxylic acid are obtained. M.p. is 234° C.

Analysis for the Formula $C_{16}H_{17}F_2N_3O_3$: Calculated: C=56.90% H=5.07% N=12.45% Found: C=57.03% H=5.11% N=12.51%.

EXAMPLE 3

According to Example 2, 1.06 g of (1-ethyl-6,7,8-trifluoro-1,4-dihydro-4-oxo-quinoline-3-carboxylate-O³,O⁴)-bis-(propionato-O)-boron are reacted with 0.64 g of piperazine in 4 ml of dimethyl sulfoxide. A 6 w/v % of aqueous solution of 6.3 ml of sodium hydroxide are added and the reaction mixture is refluxed for an hour. After filtration the pH value is adjusted to 7 with 96 w/v % acetic acid, 10 ml of water are added and the reaction mixture is cooled overnight. The precipitated crystals are filtered, washed with water and dried. Thus 0.74 g of 1-ethyl-6,8-difluoro-1,4-dihydro-4-oxo-7-piperazino-quinoline-3-carboxylic acid are obtained. M.p. is 232°–236° C.

Analysis for the formula $C_{16}H_{17}F_2N_3O_3$: Calculated: C=56.90% H=5.07% N=12.45% Found: C=56.85% H=5.00% N=12.39%.

EXAMPLE 4

According to Example 1, 1.59 g of (1-ethyl-6,7,8-trifluoro-1,4-dihydro-4-oxo-quinoline-3-carboxylate-O³,O⁴)-difluoro-boron are reacted with 1.5 g of 1-methyl-piperazine in 8 ml of dimethyl sulfoxide. Thus 1.54 g of 1-ethyl-6,8-difluoro-1,4-dihydro-4-oxo-7-(1-methyl-piperazino)-quinoline-3-carboxylic acid are obtained. M.p. is 237°–240° C.

Analysis for the Formula $C_{17}H_{19}F_2N_3O_3$: Calculated: C=58.10% H=5.45% N=11.91% Found: C=58.00% H=5.46% N=11.95%.

EXAMPLE 5

According to Example 2, 1.99 g of (1-ethyl-6,7,8-trifluoro-1,4-dihydro-4-oxo-quinoline-3-carboxylate-O³,O⁴)-bis-(acetato-O)-boron are reacted with 1.5 g of 1-methyl-piperazine. Thus 1.5 g of 1-ethyl-6,8-difluoro-1,4-dihydro-4-oxo-7-1-methyl-piperazino)-quinoline-3-carboxylic acid are obtained. M.p. is 238°–240° C.

Analysis for the formula $C_{17}H_{19}F_2N_3O_3$: Calculated: C=58.10% H=5.45% N=11.91 Found: C=58.19% H=5.53% N=11.87%.

EXAMPLE 6

According to Example 3, 1.06 g of (1-ethyl-6,7,8-trifluoro-1,4-dihydro-4-oxo-quinoline-3-carboxylate-O³,O⁴)-bis-(propionato-O)-boron are reacted with 0.75 g of 1-methyl-piperazine. Thus 0.79 g of 1-ethyl-6,8-difluoro-1,4-dihydro-4-oxo-7-(1-methyl-piperazino)-quinoline-3-carboxylic acid are obtained. M.p. is 239°–240° C.

Analysis for the Formula $C_{17}H_{19}F_2N_3O_3$: Calculated: C=58.10% H=5.45% N=11.91% Found: C=57.95% H=5.37% N=11.90%.

EXAMPLE 7

0.46 g of 1-(4'-fluoro-phenyl)-6-fluoro-7-chloro-1,4-dihydro-4-oxo-quinoline-3-carboxylate-O³,O⁴)-bis-(acetato-O)-boron are reacted with 0.6 g of N-methyl-piperazine in 5 ml of dimethyl sulfoxide at 110° C. for an hour. 10 ml of 5 w/v % aqueous sodium hydrogen carbonate solution are added, the reaction mixture is refluxed for 2 hours whereupon the pH value is adjusted to 7 with 96 w/v % acetic acid. The reaction mixture is cooled and the precipitated crystals are filtered and washed with cold water. Thus 3.54 g of 1-(4'-fluoro-phenyl)-6-fluoro-7-(N-methyl-piperazinyl)-1,4-dihydro-4-oxo-quinoline-3-carboxylic acid are obtained. M.p. is 282°–284° C. The carboxylic acid thus obtained is dissolved in a weak solution of hydrochloric acid under heating, the solution is evaporated in vacuo and thus the hydrochloric salt of 1-(4'-fluoro-phenyl)- 6-fluoro-7-(H-methyl-piperazinyl)-1,4-dihydro-4-oxo-quinoline-3-carboxylic acid is obtained.

The product decomposes over 270° C.

Analysis for the Formula $C_{21}H_{19}F_2N_3O_3$: Calculated: C=63.15% H=4.79% N=10.52% Found: C=63.27% H=4.89% N=10.35%.

We claim:

1. Process for the preparation of compounds of the Formula I

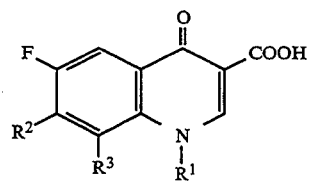

wherein
$R^1$ stands for phenyl substituted by 1 or 2 halogen atoms;
$R^2$ stands for piperazinyl or 4-methyl-piperazinyl;
$R^3$ stands for hydrogen;
or a pharmaceutically acceptable salt thereof which comprises reacting a compound of the Formula II

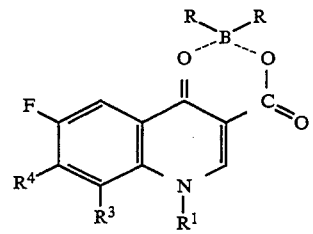

wherein R stands for halogen or an aliphatic acyloxy group containing 2 to 6 carbon atoms or an aromatic acyloxy group containing 7 to 11 carbon atoms, $R^4$ stands for fluorine or chlorine with a piperazine derivative of the Formula III

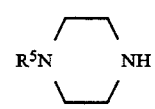

wherein $R^5$ stands for hydrogen or methyl or a salt thereof and subjecting the compound of the Formula IV

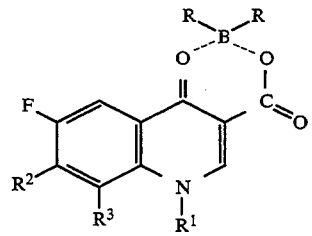

thus obtained to hydrolysis after or without isolation and if desired converting the compound of the Formula I thus obtained into a salt thereof or setting free the same from its salt.

2. Process according to claim 1 which comprises reacting a compound of the formula II with an amine of the Formula III in the presence of an organic solvent.

3. Process according to claim 2 which comprises using dimethyl sulfoxide as organic solvent.

4. Process according to claim 1 which comprises carrying out the reaction of the compounds of the Formulae II and III in the presence of an acid binding agent.

5. Process according to claim 4 which comprises using an amine or an excess of the compound of the Formula (III) as acid binding agent.

6. Process according to claim 1 which comprises carrying out the hydrolysis in acidic medium.

7. Process according to claim 6 which comprises carrying out the reaction by using an organic or inorganic acid.

8. Process according to claim 1 which comprises carrying out the hydrolysis in alkaline medium.

9. Process according to claim 8 which comprises using an alkaline metal hydroxide, an alkaline earth metal hydroxide or an organic base.

* * * * *